United States Patent [19]
Jelley et al.

[11] Patent Number: 5,889,008
[45] Date of Patent: Mar. 30, 1999

[54] SUBSTITUTED 1-INDOLYLPROPYL-4-PHENETHYLPIPERAZADINE DERIVATIVES

[75] Inventors: Richard Alexander Jelley, Sawbridgworth; Angus Murray MacLeod, Bishops Stortford; Austin John Reeve, Great Dunmow; Francine Sternfeld, London; Leslie Joseph Street, Harlow, all of United Kingdom

[73] Assignee: Merck Sharp & Dohme, Ltd., Hoddesdon, England

[21] Appl. No.: 11,308

[22] PCT Filed: Jul. 29, 1996

[86] PCT No.: PCT/GB96/01806

§ 371 Date: Feb. 5, 1998

§ 102(e) Date: Feb. 5, 1998

[87] PCT Pub. No.: WO97/06159

PCT Pub. Date: Feb. 20, 1997

[30] Foreign Application Priority Data

| Aug. 7, 1995 | [GB] | United Kingdom | 9516150 |
| Oct. 5, 1995 | [GB] | United Kingdom | 9520513 |
| Nov. 14, 1995 | [GB] | United Kingdom | 9523251 |

[51] Int. Cl.$^6$ .................... A61K 31/495; C07D 403/14; C07D 413/14; C07D 471/04

[52] U.S. Cl. .................... 514/253; 544/366; 544/369; 544/370

[58] Field of Search .................... 544/366, 369, 544/370; 514/253

[56] References Cited

FOREIGN PATENT DOCUMENTS

| 464558 | 1/1992 | European Pat. Off. . |
| 548813 | 6/1993 | European Pat. Off. . |
| 9402477 | 2/1994 | WIPO . |
| 9506636 | 3/1995 | WIPO . |
| 9532196 | 11/1995 | WIPO . |

*Primary Examiner*—Emily Bernhardt
*Attorney, Agent, or Firm*—Philippe L. Durette; Melvin Winokur

[57] ABSTRACT

A class of 1-[3-(1H-indol-3-yl)propyl]-4-(2-phenylethyl) piperazine derivatives, substituted at the 5-position of the indole nucleus by a five-membered heteroaromatic moiety, and on the phenyl ring of the phenethyl moiety by fluoro, chloro, trifluoromethyl, alkoxy or an oxazolidinone group and optionally by one or two further substituents, are selective agonists of 5-HT$_1$-like receptors, being potent agonists of the human 5-HT$_{1D}\alpha$ receptor subtype while possessing at least a 10-fold selective affinity for the 5-HT$_{1D}\alpha$ receptor subtype relative to the 5-HT$_{1D}\alpha$ subtype; they are therefore usefull in the treatment and/or prevention of clinical conditions, in particular migraine and associated disorders, for which a subtype-selective agonist of 5-HT$_{1D}$ receptors is indicated, while eliciting fewer side-effects, notably adverse cardiovascular events, than those associated with non-subtype-selective 5-HT$_{1D}$ receptor agonists.

17 Claims, No Drawings

SUBSTITUTED 1-INDOLYLPROPYL-4-PHENETHYLPIPERAZADINE DERIVATIVES

The present invention relates to a class of substituted piperazine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent application 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted piperazine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the alkoxypyridine or alkoxypyrimidine substituent with a substituted phenylethyl moiety; nor is there any suggestion therein that the range of substituents specified at the 5-position of the indole moiety might be replaced by an imidazole or triazole ring.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype. Moreover, the compounds in accordance with this invention possess interesting properties in terms of their efficacy and/or bioavailability.

The present invention provides a compound of formula I, or a salt or prodrug thereof:

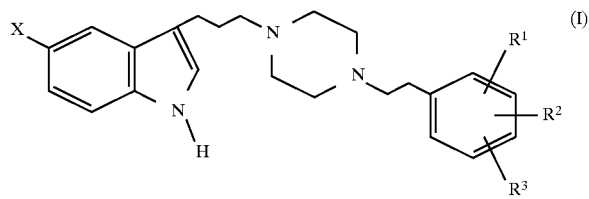

wherein

X represents a group of formula (Xa), (Xb) or (Xc):

in which Y represents nitrogen or C—R$_4$;

R$^1$ represents fluoro, chloro, trifluoromethyl, C$_{1-6}$ alkoxy or a group of formula (a):

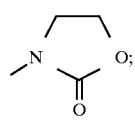

$R^2$ and $R^3$ independently represent hydrogen, halogen, trifluoromethyl or $C_{1-6}$ alkoxy; and $R^4$ represents hydrogen or $C_{1-6}$ alkyl.

The present invention also provides a compound of structural formula I above, or a salt or prodrug thereof, wherein X represents a group of formula (Xa) as defined above, and $R^1$, $R^2$ and $R^3$ are as defined above.

The compounds in accordance with the present invention are encompassed within the generic scope of co-pending International Patent Application No. PCT/GB95/01129, published as WO 95/32196 on 30 Nov. 1995. There is, however, no specific disclosure therein of compounds corresponding to those of formula I as defined above.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy" are to be construed accordingly.

The term "halogen" as used herein includes fluorine, chlorine, bromine and iodine, especially fluorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Particular acid addition salts of the compounds in accordance with the invention include the oxalate and maleate salts, typically the hydrogen oxalate and dihydrogen maleate salts, and especially the dihydrogen maleate salt. A preferred class of acid addition salts of the compounds according to the present invention comprises the citrate salts, in particular the dicitrate salt.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I above, the moiety X preferably represents a group of formula (Xa) as depicted above.

Suitably, the variable Y in formula (Xc) represents nitrogen, CH or C-methyl.

In the compounds of formula I above, the moiety $R^1$ suitably represents fluoro, trifluoromethyl, methoxy or a group of formula (a) as defined above. Particular values of $R^1$ include fluoro and trifluoromethyl, especially fluoro.

Suitably, $R^2$ and $R^3$ independently represent hydrogen, fluoro, trifluoromethyl or methoxy, in particular hydrogen or fluoro. Suitably, one or both of $R^2$ and $R^3$ represents hydrogen.

Suitably, $R^4$ represents hydrogen or methyl.

A particular sub-class of compounds according to the invention is represented by the compounds of formula IIA, and salts and prodrugs thereof:

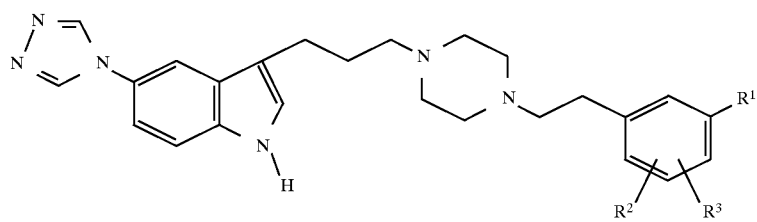

wherein $R^1$, $R^2$ and $R^3$ are as defined above.

Another sub-class of compounds according to the invention is represented by the compounds of formula IIB, and salts and prodrugs thereof:

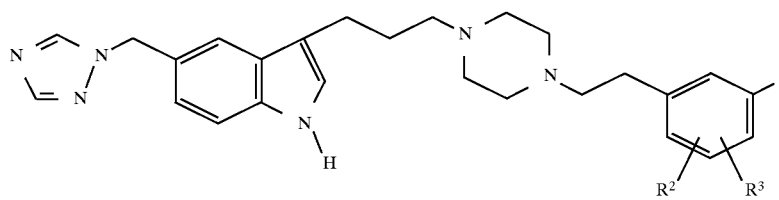

wherein $R^1$, $R^2$ and $R^3$ are as defined above.

A further sub-class of compounds according to the invention is represented by the compounds of formula IIC, and salts and prodrugs thereof:

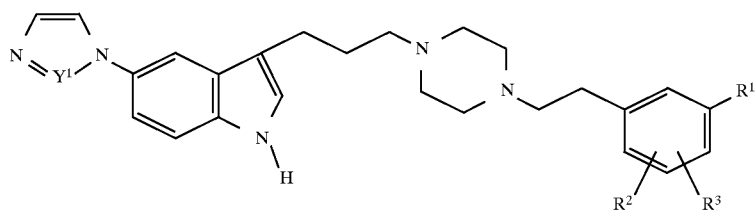

(IIC)

wherein $Y^1$ represents nitrogen, CH or C-methyl; and $R^1$, $R^2$ and $R^3$ are as defined above.

Particular values of $R^1$ in relation to formulae IIA, IIB and IIC above include fluoro and trifluoromethyl, especially fluoro.

In one embodiment of the compounds of formulae IIA, IIB and IIC above, $R^2$ is hydrogen and $R^3$ is other than hydrogen.

In another embodiment of the compounds of formulae IIA, IIB and IIC above, $R^2$ and $R^3$ are both hydrogen.

In relation to formula IIC, $Y^1$ is suitably CH or C-methyl.

Specific compounds within the scope of the present invention include:

1-[3-(5-(1,2,4-triazol-4-yl)-1H-indol-3-yl)propyl]-4-[2-(3-fluorophenyl)-ethyl]piperazine;
1-[3-(5-(1,2,4-triazol-4-yl)-1H-indol-3-yl)propyl]-4-[2-(2-fluorophenyl)-ethyl]piperazine;
1-[3-(5-(1,2,4-triazol-4-yl)-1H-indol-3-yl)propyl]-4-[2-(4-fluorophenyl)-ethyl]piperazine;
1-[3-(5-(1,2,4-triazol-4-yl)-1H-indol-3-yl)propyl]-4-[2-(3-methoxyphenyl)-ethyl]piperazine;
1-[3-(5-(1,2,4-triazol-4-yl)-1H-indol-3-yl)propyl]-4-[2-(3-trifluoromethylphenyl)ethyl]piperazine;
1-[3-(5-(1,2,4-triazol-4-yl)-1H-indol-3-yl)propyl]-4-[2-(3,4-difluorophenyl)-ethyl]piperazine;
1-[3-(5-(1,2,4-triazol-4-yl)-1H-indol-3-yl)propyl]-4-[2-(2,4-difluorophenyl)-ethyl]piperazine;
1-[3-(5-(1,2,4-triazol-4-yl)-1H-indol-3-yl)propyl]-4-[2-(3,5-difluorophenyl)-ethyl]piperazine;
1-[3-(5-(1,2,4-triazol-4-yl)-1H-indol-3-yl)propyl]-4-[2-(3-(oxazolidin-2-on-3-yl)phenyl)ethyl]piperazine;
1-[3-(5-(imidazol-1-yl)-1H-indol-3-yl)propyl]-4-[2-(3,4-difluorophenyl)-ethyl]piperazine;
1-[3-(5-(imidazol 1-yl)-1H-indol-3-yl)propyl]-4-[2-(3-fluorophenyl)-ethyl]piperazine;
1-[3-(5-(2-methylimidazol-1-yl)-1H-indol-3-yl)propyl]-4-[2-(3-fluorophenyl)ethyl]piperazine;
1-[3-(5-(1,2,4-triazol-1-ylmethyl)-1H-indol-3-yl)propyl]-4-[2-(3,4-difluorophenyl)ethyl]piperazine;
1-[3-(5-(2-methylimidazol-1-yl)-1H-indol-3-yl)propyl]-4-[2-(3,4-difluorophenyl)ethyl]piperazine;
1-[3-(5-(1,2,4-triazol-1-ylmethyl)-1H-indol-3-yl)propyl]-4-[2-(3-fluorophenyl)ethyl]piperazine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic.acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention may be prepared by a process which comprises reacting a compound of formula III with a compound of formula IV:

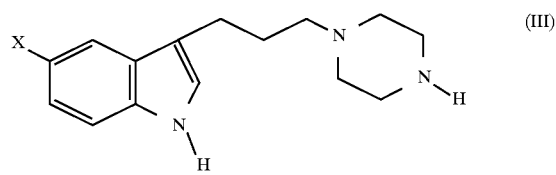

(III)

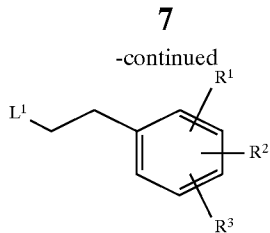

wherein X, $R^1$, $R^2$ and $R^3$ are as defined above, and $L^1$ represents a suitable leaving group.

The leaving group $L^1$ is suitably a halogen atom, e.g. chlorine or bromine, or an alkylsulphonyloxy or arylsulphonyloxy group, e.g. methanesulphonyloxy (mesyloxy) or p-toluenesulphonyloxy (tosyloxy).

The reaction between compounds III and IV is conveniently effected by stirring the reactants under basic conditions in a suitable solvent, for example triethylamine or potassium carbonate in N,N-dimethylformamide or in isopropanol and/or 1,2-dimethoxyethane, typically in the presence of sodium iodide.

In another procedure, the compounds according to the invention may be prepared by a process which comprises reacting a compound of formula III as defined above with a compound of formula V:

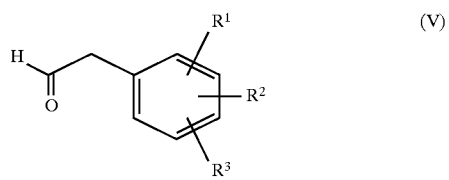

wherein $R^1$, $R^2$ and $R^3$ are as defined above; in the presence of a reducing agent.

A suitable reducing agent for effecting this process is sodium cyanoborohydride, and the reaction is conveniently carried out in methanol, typically in the presence of acetic acid, at room temperature.

In a further procedure, the compounds according to the invention may be prepared by a process which comprises reacting a compound of formula III as defined above with a carboxylic acid derivative of formula VI:

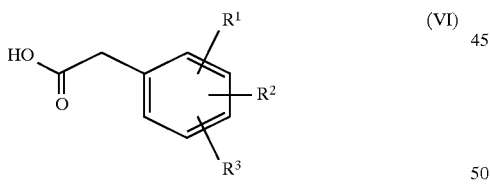

wherein $R^1$, $R^2$ and $R^3$ are as defined above; in the presence of a condensing agent; followed by treatment with a reducing agent such as diisobutylaluminium hydride.

A suitable condensing agent for use in conjunction with the above process comprises 1-(3-dimethylaminopropyl)-3-ethylcarbodiimide and 1-hydroxybenzotriazole hydrate.

The compounds of formula III above may be prepared by a process which comprises reacting the appropriate compound of formula VII:

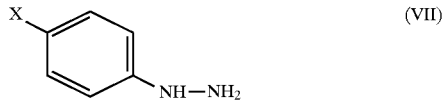

wherein X is as defined above; with a compound of formula VIII, or a carbonyl-protected form thereof:

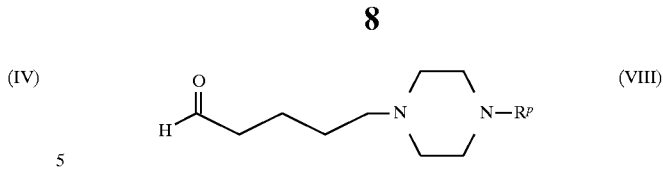

wherein $R^p$ represents an amino-protecting group; with subsequent removal of the amino-protecting group $R^p$.

The reaction between compounds VII and VIII, which is an example of the well-known Fischer indole synthesis, is suitably carried out by heating the reagents together under mildly acidic conditions, e.g. 4% sulphuric acid at reflux.

Suitable carbonyl-protected forms of the compounds of formula VIII include the dimethyl acetal derivatives.

The protecting group $R^p$ in the compounds of formula VIII is suitably a carbamoyl moiety such as tert-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds VII and VIII may be carried out in a single step, or may proceed via an initial non-cyclising step at a lower temperature to give an intermediate of formula IX:

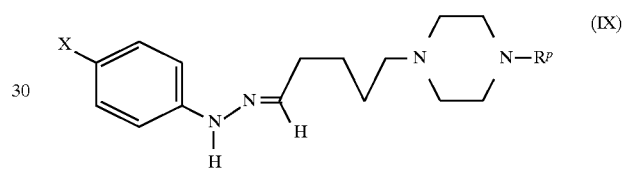

wherein X and $R^p$ are as defined above; followed by cyclisation using a suitable reagent, e.g. a polyphosphate ester.

The intermediates of formula VIII, or carbonyl-protected forms thereof, may be prepared by reacting a compound of formula X, or a carbonyl-protected form thereof, with a compound of formula XI:

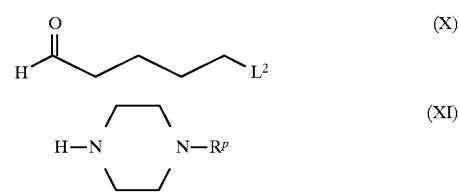

wherein $R^p$ is as defined above, and $L^2$ represents a suitable leaving group.

The leaving group $L^2$ issuitably a halogen atom, e.g. chlorine or bromine.

Where $L^2$ represents a halogen atom, the reaction between compounds X and XI is conveniently effected by stirring the reactants under basic conditions in a suitable solvent, for example potassium carbonate in 1,2-dimethoxyethane or N,N-dimethylformamide, or triethylamine in tetrahydrofuran or acetonitrile, typically in the presence of sodium iodide.

The compounds according to the invention may alternatively be prepared by a process which comprises reacting the appropriate compound of formula VII as defined above with a compound of formula XII, or a carbonyl-protected form thereof:

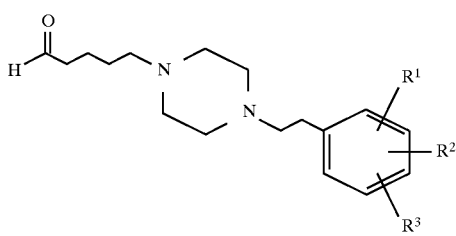
(XII)

wherein $R^1$, $R^2$ and $R^3$ are as defined above; under conditions analogous to those described above for the reaction between compounds VII and VIII.

As for the compounds of formula VIII, suitable carbonyl-protected forms of the compounds of formula XII include the dimethyl acetal derivatives.

As with that between compounds VII and VIII, the Fischer reaction between compounds VII and XII may be carried out in a single step, or may proceed via an initial non-cyclising step at a lower temperature to give an intermediate of formula XIII:

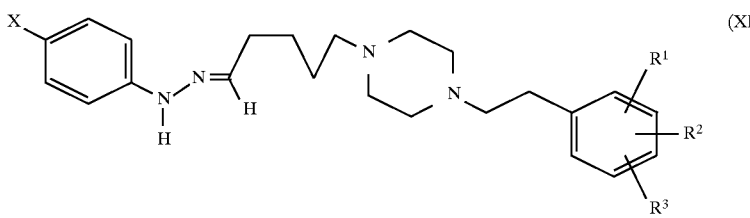
(XIII)

wherein X, $R^1$, $R^2$ and $R^3$ are as defined above; followed by cyclisation using a suitable reagent, e.g. a polyphosphate ester.

The intermediates of formula XII, or carbonyl-protected forms thereof, may be prepared by reacting a compound of formula X as defined above, or a carbonyl-protected form thereof, with a compound of formula XIV:

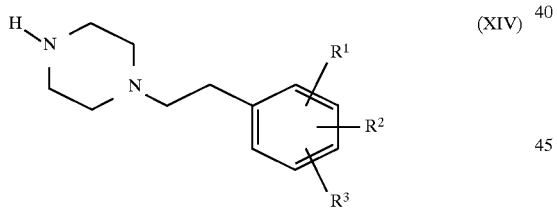
(XIV)

wherein $R^1$, $R^2$ and $R^3$ are as defined above; under conditions analogous to those described above for the reaction between compounds X and XI In an alternative procedure, the compounds of formula III above may be prepared by a process which comprises reacting a compound of formula $X^1$ as defined above with a compound of formula XV:

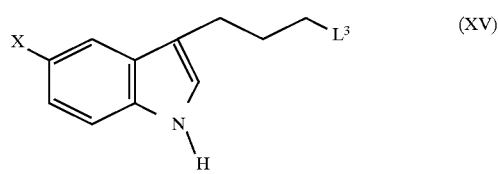
(XV)

wherein X is as defined above, and $L^3$ represents a suitable leaving group; followed by removal of the amino-protecting group $R^p$.

Similarly, the compounds of formula I as defined above may be prepared by a process which comprises reacting a compound of formula XIV as defined above with a compound of formula XV as defined above.

The leaving group $L^3$ is suitably an alkylsulphonyloxy or arylsulphonyloxy group, e.g. methanesulphonyloxy (mesyloxy) or p-toluenesulphonyloxy (tosyloxy).

Where $L^3$ represents an alkylsulphonyloxy or arylsulphonyloxy group, the reaction between compound XV and compound XI or XIV is conveniently carried out in a suitable solvent such as tetrahydrofuran, 1,2-dimethoxyethane or isopropyl alcohol, typically in the presence of a base such as sodium carbonate or potassium carbonate, optionally with the addition of sodium iodide.

In one representative approach, the compounds of formula XV wherein $L^3$ represents a mesyloxy or tosyloxy group may be prepared by the sequence of steps illustrated in the following reaction scheme (cf. Larock and Yum, *J. Am. Chem. Soc.*, 1991; 113, 6689):

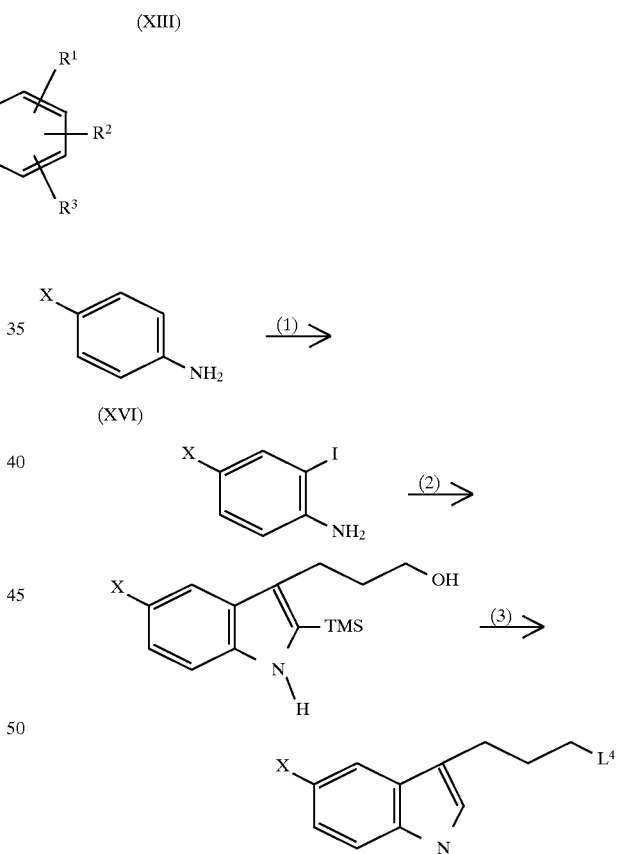

wherein X is as defined above, $L^4$ represents mesyloxy or tosyloxy, and TMS is an abbreviation for trimethylsilyl.

In Step 1 of the reaction scheme, the aniline derivative XVI is treated with iodine monochloride, advantageously in methanol in the presence of a base such as calcium carbonate, in order to introduce an iodine atom ortho to the amine moiety. Step 2 involves a palladium-mediated coupling reaction with the protected acetylene derivative TMS—C≡C—(CH$_2$)$_3$—OH, typically using palladium acetate and triphenylphosphine in the presence of lithium chloride and sodium carbonate, suitably in N,N-dimethylformamide at an elevated temperature. This is followed in Step 3 by removal of the TMS moiety, ideally in refluxing methanolic hydrochloric acid; followed in turn by mesylation or tosylation, suitably by using mesyl chloride or tosyl chloride respectively, in pyridine or triethylamineltetrahydrofuran.

In another representative approach, the compounds of formula XV wherein $L^3$ represents a mesyloxy or tosyloxy group may be prepared by reacting 3,4-dihydro-2H-pyran with the appropriate compound of formula VII as defined above or a salt thereof, under a variant of the Fischer reaction conditions as described above for the reaction between compounds VII and VIII; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating the appropriate hydrazine derivative VII or an acid addition salt thereof, typically the hydrochloride salt, in an inert solvent such as dioxan, advantageously in the presence of a mineral acid such as hydrochloric acid or a Lewis acid such as zinc chloride, at the reflux temperature of the solvent.

In a yet further procedure, the compounds of formula III above may be prepared by a process which comprises reducing a compound of formula XVII:

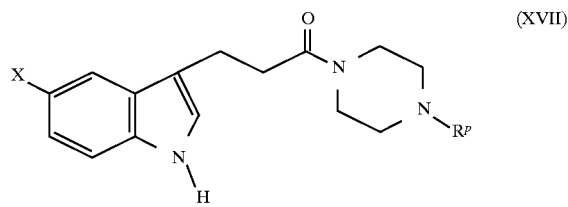

(XVII)

wherein X and $R^p$ are as defined above; with subsequent removal of the amino-protecting group $R^p$.

Similarly, the compounds according to the invention may be prepared by a process which comprises reducing a compound of formula XVIII:

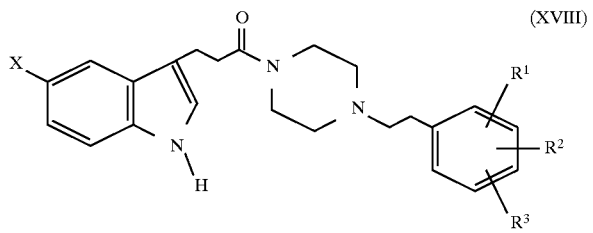

(XVIII)

wherein X, $R^1$, $R^2$ and $R^3$ are as defined above.

The reduction of compound XVII or compound XVIII is conveniently effected by treating the appropriate compound with a reducing agent such as lithium aluminium hydride in an appropriate solvent, e.g. diethyl ether or tetrahydrofuran, or mixtures thereof.

The compounds of formulae XVII and XVIII above may suitably be prepared by reacting the appropriate compound of formula XI or XIV with a compound of formula XIX:

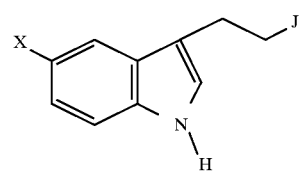

(XIX)

wherein X is as defined above, and J represents a reactive carboxylate moiety.

Suitable values for the reactive carboxylate moiety J include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XIX above wherein J is an acid chloride moiety may be prepared by treating the corresponding carboxylic acid derivative with thionyl chloride in toluene. Similarly, the intermediates of formula XIX wherein J is an acylimidazole moiety may be prepared by treating the corresponding carboxylic acid derivative with 1,1'-carbonyldiimidazole. Alternatively, the reactive carboxylate moiety J may be obtained by treating the corresponding compound wherein J is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula XI or XV.

The hydrazine derivatives of formula VII above can be prepared by the methods described in EP-A-0497512 and WO-A-94/03446, as also can the aniline derivatives of formula XVI.

Where they are not commercially available, the starting materials of formula IV, V, VI, X, XI, XIV and XIX may be prepared by methods analogous to those described in the accompanying Examples, or by standard procedures well known from the art.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-HT$_{1D\alpha}$ receptor subtype, inhibit forskolin-stimulated adenylyl cyclase activity, and stimulate [$^{35}$S]-GTPγS binding to membranes from clonal cell lines expressing human cloned receptors.

5-HT$_{1D\alpha}$/5-HT$_{1D\beta}$ Radioligand Binding

Chinese hamster ovary (CHO) clonal cell lines expressing the human 5-HT$_{1D\alpha}$ and 5-HT$_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, CaCl$_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM was used to define non-specific binding. The reaction was initiated by the addition of membrane and was terminated by rapid filtration through Whatman GF/B filters (presoaked in 0.3% PEI/ 0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which IC$_{50}$ (the molar concentration of compound necessary to inhibit binding by 50%) values could be calculated for each test compound. The IC$_{50}$ values for binding to the 5-HT$_{1D\alpha}$ receptor subtype obtained for the compounds of the accompanying Examples were below 50 nM in each case. Furthermore, the compounds of the accompanying Examples were all found to possess a selective affinity for the 5-HT$_{1D\alpha}$ receptor subtype of at least 10-fold relative to the 5-HT$_{1D\beta}$ subtype.

5-HT$_{1D\alpha}$/5-HT$_{1D\beta}$ Adenylyl Cyclase Assay

Studies were performed essentially as described in *J. Pharmacol. Exp. Ther.*, 1986, 238, 248. CHO clonal cell lines expressing the human cloned 5-HT$_{1D\alpha}$ and 5-HT$_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 βM, in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM MgCl$_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D\alpha}$ receptor subtype relative to the 5-HT$_{1D\beta}$ subtype.

5-HT$_{1D\alpha}$/5-HT$_{1D\beta}$ GTPγS Binding

Studies were performed essentially as described in *Br. J. Pharmacol.*, 1993, 109, 1120. CHO clonal cell lines expressing the human cloned 5-HT$_{1D\alpha}$ and 5-HT$_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, MgCl$_2$ 10, pargyline 0.01; ascorbate 0.1%; pH 7.4 at room temperature) at a concentration of 40 μg protein/ml for the 5-HT$_{1D\alpha}$ receptor transfected cells and 40–50 μg protein/ml for the 5-HT$_{1D\beta}$ receptor transfected cells. The membrane suspension was then incubated, in a volume of 1 ml, with GDP (100 μM for 5-HT$_{1D\alpha}$ receptor transfected cells, 30 μM for the 5-HT$_{1D\beta}$ receptor transfected cells) and test compound at 30° C. for 20 min and then transferred to ice for a further 15 min. [35S]-GTPYS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which E$_{max}$ (maximal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D\alpha}$ receptor subtype relative to the 5-HT$_{1D\beta}$ subtype.

EXAMPLE 1

1-[3-(5-(1,2,4-Triazol-4-yl)-1H-indol-3-yl)propyl]-4-[2-(3-fluorophenyl)-ethyl]piperazine. 1.4 Hydrogen Oxalate. Monohydrate-0.2 Diethyl etherate 1. Intermediate 1:4-(1,2,4-Triazol-4-yl)phenylhydrazine
   Prepared as described in WO 94/03446, Example 1.
2. Intermediate 2:1-[3-(5-(1,2,4-Triazol-4-yl)-1H-indol-3-yl)propyl]-4-(H)-piperazine. 3.5 Hydrogen Oxalate
(i) 5-(4-tert-Butyloxycarbonyl)piperazin-1-yl pentanal dimethyl acetal
a) 5-Bromopentanal dimethyl acetal To a solution of 5-bromovaleryl chloride (50 g, 0.251 mol) in anhydrous THF (500 ml), at −78° C., was added lithium tri-tert-butoxyaluminohydride (1.0 M solution in tetrahydrofuran, 300 ml; 0.30 mol), keeping the temperature below −70° C. The solution was stirred at −78° C. for 5 h and then quenched by dropwise addition of 2M hydrochloric acid (350 ml). The mixture was warmed to room temperature and stirred for 16 h. Diethyl ether (500 ml) was added, the aqueous phase separated and extracted further with ether (×2). The combined extracts were washed with saturated $Na_2CO_3$ solution (×1), water (×1) and brine (×2), dried ($Na_2SO_4$) and evaporated to give 5-bromovaleraldehyde (37.5 g, 91%). A solution of 5-bromovaleraldehyde (37.5 g, 0.227 mol) in methanol (250 ml) and concentrated sulphuric acid (0.5 ml) was stirred at room temperature for 3 h. The solvent was removed under vacuum and to the residue was added $K_2CO_3$ solution (50 ml) and diethyl ether (500 ml). The aqueous layer was separated and re-extracted with ether (×2). The combined extracts were washed with water and brine, dried ($Na_2SO_4$) and evaporated. The crude product was chromatographed on silica gel eluting with diethyl ether/hexane (1:9) to give the title-acetal (27.5 g, 57%). δ (250 MHz, $CDCl_3$) 1.43–1.67 (4H, m, 2 of $CH_2$); 1.83–1.94 (2H, m, $CH_2$); 3.38 (6H, s, $CH(OMe)_2$); 3.42 (2H, t, J=7 Hz, $CH_2Br$), 4.37 (1H, t, J=7 Hz, $CH(OMe)_2$).

b) 5-(4-tert-Butyloxycarbonyl)piperazin-1-yl pentanal dimethyl acetal

A mixture of 5-bromovaleraldehyde dimethyl acetal (27.5 g, 0.13 mol), $Na_2CO_3$ (20.7 g, 0.195 mol), sodium iodide (19.5 g, 0.13 mol) and tert-butyl-1-piperazinecarboxylate (25.5 g, 0.137 mol), in dimethoxyethane (250 ml), was heated at 100° C. for 3 h. Aluminium foil was wrapped around the vessel to exclude light. The mixture was cooled to room temperature and filtered. The filtrate was evaporated under reduced pressure and then EtOAc (50 ml) added and the mixture filtered again to remove inorganic salts. The solvent was removed under vacuum and the residue chromatographed on silica gel eluting with EtOAc to give the title-product (25.7 g, 63%). δ (250 MHz, $CDCl_3$) 1.29–1.71 (6H, m, 3 of $CH_2$); 1.46 (9H, s, $OC(Me)_3$); 2.31–2.39 (6H, m, 3 of $CH_2$); 3.32 (6H, s, $CH(OMe)_2$); 3.41–3.45 (4H, m, 2 of $CH_2$); 4.36 (1H, t, J=6 Hz, $CH(OMe)_2$).

(ii) 1-[3-(5-(1,2,4-Triazol-4-yl)-1H-indol-3-yl)propyl]-4-(H)-piperazine. 3.5 Hydrogen Oxalate A mixture of Intermediate 1 (5.0 g, 28.6 mmol) and 5-(4-tert-butyloxycarbonyl)piperazin-1-yl pentanal dimethyl acetal (9.03 g, 28.6 mmol) in 4% sulphuric acid (150 ml) was heated at reflux for 48 h. The solution was cooled in an ice-bath, basified with solid $K_2CO_3$ and extracted with butan-1-ol (×3). The solvent was removed under vacuum and azeotroped with hexane (×2). The crude product was purified by chromatography on silica gel eluting with $CH_2Cl_2$/MeOH/$NH_3$ (30:8:1) to give the title-indole (3.9 g, 44%). The 3.5 hydrogen oxalate salt was prepared using 200 mg of free base: mp 90°–92° C. (Found: C, 45.97; H, 4.76; N, 13.77. $C_{17}H_{22}N_6$.3.5($C_2H_2O_4$) requires C, 46.08; H, 4.76; N, 13.43%); δ (360 MHz, $D_2O$) 2.12–2.24 (2H, m, $CH_2$); 2.93 (2H, t, J=7 Hz, $CH_2$); 3.46–3.76 (8H, m, 4 of $CH_2$); 7.37 (1H, dd, J=1.9 and 8.7 Hz, Ar—H); 7.39 (1H, s, Ar—H); 7.66 (1H, d, J=8.7 Hz, Ar—H); 7.82 (1H, d, J=1.9 Hz, Ar—H); 9.13 (2H, s, Triazole-H).

3. Intermediate 3:3-(Fluoro)phenethyl bromide a) 3-(Fluoro)phenethyl alcohol

To a stirred solution of 3-fluorophenylacetic acid (5.0 g, 32.0 mmol) in diethyl ether (100 ml), at −10° C., was added lithium aluminium hydride (32.4 ml of a 1M solution in diethyl ether, 32.4 mmol), dropwise. The reaction mixture was allowed to warm to +25° C. and stirred for 1 h, before again cooling to −10° C., and quenching by addition of methanol (20 ml) and 4M sodium hydroxide (20 ml). The resulting slurry was filtered and the filtrate evaporated in vacuo. The crude product was chromatographed on silica gel eluting with $CH_2Cl_2$/MeOH/$NH_3$ (80:8:1) to give 3-(fluoro)phenethyl alcohol (3.80 g, 84%), δ (250 MHz, $CDCl_3$) 2.87 (3H, t, J=6.5 Hz, $CH_2$), 3.87 (3H, t, J=6.5 Hz, $CH_2$), 6.89–7.02 (3H, m, Ar—H), 7.23–7.33 (1H, m, Ar—H).

b) 3-(Fluoro)phenethyl bromide

To a solution of 3-(fluoro)phenethyl alcohol (3.8 g, 27.0 mmol), in anhydrous dichloromethane (100 ml), cooled to 0° C., was added carbon tetrabromide (11.25 g, 34.0 mmol) and triphenylphosphine (10.62 g, 41.0 mmol). After stirring for 0.5 h the solvent was removed in vacuo and diethyl ether (100 ml) was added to the residue. The resultant precipitate was removed by filtration, the filtrate evaporated under reduced pressure and the crude product chromatographed on silica-gel eluting with ethyl acetate/hexane (1:1) to give 3-(fluoro)phenethyl bromide (5.51 g, 100%), δ (250 MHz, $CDCl_3$) 3.16 (2H, t, J=7.4 Hz, $CH_2$), 3.57 (2H, t, J=7.4 Hz, $CH_2$), 6.91–7.01 (3H, m, Ar—H), 7.24–7.33 (1H, m, Ar—H).

4. 1-[3-(5-(1,2,4-Triazol-4-yl)-1H-indol-3-yl)propyl]-4-[2-(3-fluorophenyl)ethyl]perazine. 1.4 Hydrogen Oxalate. Monohydrate-0.2 Diethyl etherate To a solution of 1-[3-(5-(1,2,4-triazol-4-yl)-1H-indol-3-yl)propyl]-4-(H)-piperazine (0.20 g, 0.65 mmol), in isopropyl alcohol (10 ml) and DME (30 ml), was added $K_2CO_3$ (0.178 g, 1.29 mmol), sodium iodide (0.10 g, 0.65 mmol) and 3-(fluoro)phenethyl bromide (0.144 g, 0.71 mmol) and the mixture refluxed for 16 h. The reaction mixture was cooled to room temperature and the solvent removed in vacuo. The residue was taken up into aqueous $K_2CO_3$ solution (20 ml) and extracted with ethyl acetate (3×). The combined extracts were dried ($MgSO_4$) and evaporated, and the residue chromatographed on silica gel, eluting with $CH_2Cl_2$/MeOH/$NH_3$ (90:8:1) to give the title-compound (66 mg, 24%). The hydrogen oxalate salt was prepared, mp 175°–176° C., (Found: C, 57.98; H, 6.18; N, 13.88. $C_{25}H_{29}N_6F$.1.4($C_2H_2O_4$).1.0$H_2O$.0.2(diethyl ether) requires C, 58.08; H, 6.10; N, 14.20%), m/e 433 (M+1)$^+$, δ (360 MHz, $D_6$-DMSO) 1.94–2.04 (2H, m, $CH_2$), 2.66–3.16 (16H, m, 8 of $CH_2$), 6.98–7.12 (3H, m, Ar—H), 7.08–7.34 (3H, m, Ar—H), 7.50 (1H, d, J=8.7 Hz, Ar—H), 7.80 (1H, d, J=2.0 Hz, Ar—H), 9.01 (2H, s, Ar—H), 11.16 (1H, s, NH).

Examples 2–5 were prepared using the procedures described for Example 1 starting from either the commercially available phenethyl alcohols or the phenylacetic acid.

EXAMPLE 2

1-[3-(5-(1,2,4-Triazol-4-yl)-1H-indol-3-yl)propyl]-4-[2-(2-fluorophenyl)ethyl]perazine. 1.6 Hydrogen Oxalate. Monohydrate. 0.3 Diethyl etherate mp: 216°–217° C., (Found: C, 57.28; H, 6.09; N, 13.25. $C_{25}H_{29}N_6F$.1.6($C_2H_2O_4$).1.0$H_2O$.0.3(diethyl ether) requires C, 57.24; H, 6.08; N, 13.62%), δ (360 MHz, $D_6$-DMSO) 1.96–2.06 (2H, m, $CH_2$), 2.66–3.20 (16H, m, 8 of $CH_2$), 7.13–7.18 (2H, m, Ar—H), 7.25–7.37 (4H, m, Ar—H), 7.51 (1H, d, J=8.7 Hz, Ar—H), 7.81 (1H, d, J=2.0 Hz, Ar—H), 9.02 (2H, s, Ar—H), 11.18 (1H, s, NH).

EXAMPLE 3

1-[3-(5-(1,2,4-Triazol-4-yl)-1H-indol-3-yl)propyl]-4-[2-(4-fluorophenyl)ethyl]piperazine. 3.4 Hydrogen Oxalate mp: 201°–202° C., (Found: C, 51.67; H, 5.05; N, 11.56. $C_{25}H_{29}N_6F$.3.4($C_2H_2O_4$) requires C, 51.71; H, 4.89; N, 11.37%), m/e 433 (M+1)$^+$, δ (250 MHz, $D_6$-DMSO) 1.90–2.06 (2H, m, $CH_2$), 2.68–3.14 (16H, m, 8 of $CH_2$), 7.08–7.14 (2H, m, Ar—H), 7.24–7.34 (4H, m, Ar—H), 7.50 (1H, d, J=8.6 Hz, Ar—H), 7.80 (1H, d, J=2.0 Hz, Ar—H), 9.02 (2H, s, Ar—H), 11.17 (1H, s, NH).

EXAMPLE 4

1-[3-(5-(1,2,4-Triazol-4-yl)-1H-indol-3-yl)propyl]-4-[2-(3-methoxyphenyl)ethyl]piperazine. 1.1 Hydrogen Oxalate. 0.7 Hydrate mp: 190°–191° C., (Found: C, 60.88; H, 6.42; N, 14.92. $C_{26}H_{32}N_6O.1.1(C_2H_2O_4).0.7H_2O$ requires C, 60.89; H, 6.45; N, 15.11%), m/e 445 (M+1)$^+$, δ (360 MHz, D$_6$-DMSO) 1.90–2.02 (2H, m, CH$_2$), 2.66–3.10 (16H, m, 8 of CH$_2$), 3.74 (3H, s, OMe), 6.75–6.82 (3H, m, Ar—H), 7.18–7.03 (1H, m, Ar—H), 7.30–7.34 (2H, m, Ar—H), 7.50 (1H, d, J=8.5 Hz, Ar—H), 7.80 (1H, d, J=2.0 Hz, Ar—H), 9.02 (2H, s, Ar—H), 11.15 (1H, s, NH).

EXAMPLE 5

1-[3-(5-(1,2,4-Triazol-4-yl)-1H-indol-3-yl)propyl]-4-[2-(3-trifluoromethylphenyl)ethyl]piperazine. 2.0 Hydrogen Oxalate. Hemihydrate mp: 223°–224° C., (Found: C, 53.57; H, 4.99; N, 12.42. $C_{26}H_{29}N_6F_3.2.0(C_2H_2O_4).0.5H_2O$ requires C, 53.65; H, 5.10; N, 12.51%), m/e 483 (M+1)$^+$, δ (360 MHz, D$_6$-DMSO) 1.94–2.05 (2H, m, CH$_2$), 2.64–3.24 (16H, m, 8 of CH$_2$), 7.30–7.33 (2H, m, Ar—H), 7.50 (1H, d, J=8.6 Hz, Ar—H), 7.51–7.58 (3H, m, Ar—H), 7.62 (1H, s, Ar—H), 7.80 (1H, d, J=2.0 Hz, Ar—H), 9.01 (2H, s, Ar—H), 11.16 (1H, s, NH).

EXAMPLE 6

1-[3-(5-(1,2,4-Triazol-4-yl)-1H-indol-3-yl)propyl]-4-[2-(3,4-difluorophenyl)ethyl]piperazine. 1.15 Hydrogen Oxalate. 0.3 Hydrate a) 3,4-(Difluoro)phenethyl bromide Prepared from 3,4-(difluoro)phenylacetic acid using the procedures described for Intermediate 3. δ (250 MHz, CDCl$_3$) 3.12 (2H, t, J=7.3 Hz, CH$_2$), 3.54 (2H, t, J=7.3 Hz, CH$_2$), 6.90–7.16 (3H, m, Ar—H).

b) 1-[3-(5-(1,2,4-Triazol-4-yl)-1H-indol-3-yl)propyl]-4-[2-(3,4-difluorophenyl)ethyl]piperazine. 1.15 Hydrogen Oxalate. 0.3 Hydrate To a solution of 1-[3-(5-(1,2,4-triazol-4-yl)-1H-indol-3-yl)propyl]-4-(H)-piperazine (0.2 g, 0.65 mmol), in anhydrous DMF (30 ml), was added anhydrous triethylamine (0.13 g, 1.29 mmol), sodium iodide (0.09 g, 0.65 mmol), and 3,4-(difluoro)phenethyl bromide (0.157 g, 0.71 mmol) and the mixture heated at reflux for 16 h. The reaction mixture was cooled to room temperature and partitioned between water (40 ml) and ethyl acetate (150 ml). The organic layer was separated and washed with water (2×) and brine (1×). The organic solution was dried (MgSO$_4$) and the solvent removed in vacuo. The crude product was chromatographed on silica gel eluting with CH$_2$Cl$_2$/MeOH/NH$_3$ (90:8:1) to give the title-compound (0.05 g, 20%). The hydrogen oxalate salt was prepared, mp 168°–169° C., (Found: C, 58.67; H, 5.62; N, 15.02. $C_{25}H_{28}N_6F_2.1.15(C_2H_2O_4).0.3H_2O$ requires C, 58.61; H, 5.57; N, 15.02%), m/e 451 (M+1)$^+$, δ (360 MHz, D$_6$-DMSO) 1.92–2.03 (2H, m, CH$_2$), 2.60–3.20 (16H, m, 8 of CH$_2$), 7.06–7.10 (1H, m, Ar—H), 7.29–9.37 (4H, m, Ar—H), 7.49 (1H, d, J=8.6 Hz, Ar—H), 7.80 (1H, d, J=2.0 Hz, Ar—H), 9.01 (2H, s, Ar—H), 11.16 (1H, s, NH).

Examples 7 and 8 were prepared using the general procedures described for Example 6.

EXAMPLE 7

1-[3-(5-(1,2,4-Triazol-4-yl)-1H-indol-3-yl)propyl]-4-[2-(2,4-difluorophenyl)ethyl]piperazine. 2.75 Hydrogen Oxalate. Hemihydrate mp: 208°–209° C., (Found: C, 51.81; H, 4.92; N, 11.88. $C_{25}H_{28}N_6F_2.2.75(C_2H_2O_4).0.5H_2O$ requires C, 52.01; H, 5.14; N, 11.86%), m/e 451 (M+1)$^+$, δ (250 MHz, D$_6$-DMSO) 1.84–2.06 (2H, m, CH$_2$), 2.50–3.18 (16H, m, 8 of CH$_2$), 6.92–7.40 (5H, m, Ar—H), 7.47 (1H, d, J=8.6 Hz, Ar—H), 7.76 (1H, d, J=2.0 Hz, Ar—H), 8.99 (2H, s, Ar—H), 11.14 (1H, s, NH).

EXAMPLE 8

1-[3-(5-(1,2,4-Triazol-4-yl)-1H-indol-3-yl)propyl]-4-[2-(3,5-difluorophenyl)ethyl]piperazine. 2.5 Hydrogen Oxalate. Hemihydrate mp: 223°–224° C., (Found: C, 52.62; H, 5.31; N, 12.09. $C_{25}H_{28}N_6F_2.2.5(C_2H_2O_4).0.5H_2O$ requires C, 52.63; H, 5.01; N, 12.27%), m/e 451 (M+1)$^+$, δ (360 MHz, D$_6$-DMSO) 1.94–2.08 (2H, m, CH$_2$), 2.68–3.16 (16H, m, 8 of CH$_2$), 6.98–7.06 (3H, m, Ar—H), 7.30–7.36 (2H, m, Ar—H), 7.51 (1H, d, J=8.6 Hz, Ar—H), 7.81 (1H, d, J=2.0 Hz, Ar—H), 9.02 (2H, s, Ar—H), 11.16 (1H, s, NH).

EXAMPLE 9

1-[3-(5-(1,2,4-Triazol-4-yl)-1H-indol-3-yl)propyl]-4-[2-(3-oxazolidin-2-on-3-yl)phenyl)ethyl]piperazine. 1.2 Hydrogen Oxalate. Monohydrate a) 3-Aminophenethyl alcohol To a solution of 3-nitrophenethyl alcohol (5.13 g, 30.7 mmol), in ethanol (100 ml), was added a slurry of 10% Pd—C (0.5 g), in water (4 ml), and the mixture hydrogenated in a Parr flask, at 45 psi for 0.75 h. The catalyst was removed by filtration and the solvent evaporated to give 3-aminophenethyl alcohol (4.2 g, 100%), mp 61°–64° C., δ (360 MHz, CDCl$_3$) 2.77 (2H, t, J=6.7 Hz, CH$_2$), 3.80 (2H, t, J=6.7 Hz, CH$_2$), 6.55–6.63 (3H, m, Ar—H), 7.08 (1H, dd, J=7.6 and 8.06 Hz, Ar—H).

b) 3-(Oxazolidin-2-on-3-yl)phenethyl alcohol

To a solution of 3-aminophenethyl alcohol (2.0 g, 14.6 mmol) in dioxane (50 ml) and water (25 ml) was added an aqueous solution of sodium hydroxide (0.64 g in 14.4 ml of water, 16.1 mmol), followed by chloroethyl chloroformate (2.19 g, 15.3 mmol). The mixture was stirred for 0.25 h at room temperature and then NaOH solution added to pH11 and stirring continued for 0.25 h. Further chloroethyl chloroformate (1.1 g, 7.7 mmol) was added followed, after 10 minutes, by NaOH solution to pH11. The mixture was stirred for 0.25 h and the solvents removed in vacuo. The residue was partitioned between ethyl acetate (2×100 ml) and water (50 ml) and the organic extracts combined, dried (Na$_2$SO$_4$) and evaporated. The residue was chromatographed on silica gel with 50% ethyl acetate/hexane to give the chloroethyl carbamate (3.6 g, 100%). To a solution of sodium (85 mg, 3.7 mmol), in methanol (10 ml), was added a solution of the preceding carbamate (0.9 g, 3.7 mmol), in methanol (10 ml), and the mixture stirred at room tempaerature for 16 h. The reaction mixture was partitioned between water (50 ml) and ethyl acetate (4×50 ml). The combined organic extract was dried (Na$_2$SO$_4$), evaporated, and the residue chromatographed on silica gel, eluting with ethyl acetate to give the title-oxcazolidinone (0.628 g, 82%), mp 82°–85° C., δ (250 MHz, CDCl$_3$) 2.90 (2H, t, J=6.5 Hz, CH$_2$), 3.89 (2H, t, J=6.5 Hz, CH$_2$), 4.04–4.10 (2H, m, CH$_2$), 4.46–4.52 (2H, m, CH$_2$), 7.03 (1H, d, J=6.8 Hz, Ar—H), 7.29–7.40 (2H, m, Ar—H), 7.48 (1H, s, Ar—H).

c) 3-(Oxazolidin-2-on-3-yl)phenethyl bromide

To a solution of the preceding alcohol (0.5 g, 2.4 mmol), in anhydrous dichloromethane (25 ml), was added triphenylphosphine (0.95 g, 3.6 mmol) and carbon tetrabromide (100 g, 3.0 mmol) and the mixture stirred at room temperature for 0.5 h. The solvent was removed under vacuum and the residue was triturated with diethyl ether. The resultant solid was removed by filtration and the filtrate evaporated. The residue was chromatographed on silica gel eluting with ethyl acetate/hexane (1:1) to give the title-bromide (0.59 g, 91%), mp 73°–75° C., δ (360 MHz, CDCl$_3$) 3.18 (2H, t, J=7.5 Hz, CH$_2$), 3.58 (2H, t, J=7.5 Hz, CH$_2$), 4.07 (2H, dd, J=6.5 and 8.3 Hz, CH$_2$), 4.49 (2H, dd, J=6.5 and 8.3 Hz, CH$_2$), 7.00 (1H, d, J=7.0 Hz, Ar—H), 7.31–7.38 (2H, m, Ar—H), 7.51 (1H, s, Ar—H).

d) 1-[3-(5-(1,2,4-Triazol-4-yl)-1H-indol-3-yl)propyl]-4-[2-(3-(oxazolidin-2-on-3-yl)phenyl)ethyl]piperazine. 1.2 Hydrogen Oxalate. Monohydrate A mixture of 1-[3-(5-(1,2,4-triazol-4-yl)-1H-indol-3-yl) propyl]-4(H)-piperazine (0.20 g, 0.65 mmol), 3-(oxazolidin-2-on-3-yl)phenethyl bromide (0.192 g, 0.71 mmol) and K$_2$CO$_3$ (98 mg, 0.71 mmol), in anhydrous DMF (5 ml), was heated at 70° C. for 1.5 h. The mixture was cooled to room temperature and the solvent removed in vacuo. The residue was partitioned between CH$_2$Cl$_2$ (2×50 ml) and water (5 ml). The combined extracts were dried (Na$_2$SO$_4$) and evaporated and the residue chromatographed on silica gel with CH$_2$Cl$_2$/MeOH (90:10→80:20) to give the title product (0.217 g, 67%). The hydrogen oxalate salt was prepared, mp 136° C. (dec.), (Found: C, 58.34; H, 6.34; N, 15.29. C$_{28}$H$_{33}$N$_7$O$_2$.1.2(C$_2$H$_2$O$_4$).1.0H$_2$O requires C, 58.36; H, 6.03; N, 15.67%), m/e 500 (M+1)$^+$, δ (250 MHz, D$_6$-DMSO) 1.88–2.06 (2H, m, CH$_2$), 2.60–3.17 (16H, m, 8 of CH$_2$), 4.04 (2H, dd, J=7.4 and 9.6 Hz, CH$_2$), 4.43 (2H, dd, J=7.4 and 9.6 Hz, CH$_2$), 7.00 (1H, d, J=7.5 Hz, Ar—H), 7.27–7.52 (6H, m, Ar—H), 7.80 (1H, d, J=2.0 Hz, Ar—H), 9.03 (2H, s, Ar—H), 11.19 (1H, s, NH.

EXAMPLE 10

1-[3-(5-(1,2,4-Triazol-4-yl)-1H-indol-3-yl) propyl]-4-[2-(3-fluorophenyl)ethyl]piderazine. Dihydrogen Maleate. 0.4 Hydrate a) 1-(3-Fluorophenyl)-2-methoxyethene Phenyllithium (98.3 ml of a 1.8M solution in cydohexane/diethyl ether, 177 mmol) was added to a stirred suspension of (methoxymethyl)triphenylphosphonium chloride (60.82 g, 177 mmol) (note—dried overnight at 50° C. in vacuo immediately prior to use), in diethyl ether (500 ml) at 0° C. under nitrogen. The solid was seen to dissolve and a bright orange/brown coloration formed. The mixture was stirred at 0° C. for 0.25 h and then at room temperature for 0.5 h. The mixture was cooled to −20° C. and 3-fluorobenzaldehyde (20.0 g, 161 mmol) then added. The reaction mixture was allowed to warm to room temperature and stirred overnight (16 h). Saturated ammonium chloride solution (250 ml) was added and the aqueous separated and extracted further with diethyl ether (×2). The combined ethereal layers were dried (MgSO$_4$), evaporated in vacuo and the residue distilled (≈60° C. at 1.3 mbar) to remove the majority of the phosphorous by-products. The distillate was then purified by column chromatography on silica gel, eluting with ethyl acetate/hexane (2:98) to give the title-enol ether as an E/Z mixture (10.7 g, 44%), δ (250 MHz,CDCl$_3$) 3.69 and 3.80 (total 3H, 2 of s, OCH$_3$), 5.21 and 5.77 (total 1H, 2 of d, J=7.0 Hz and 13.0 Hz respectively, C=CHz and C=CHe), 6.18 (d, J=7.0 Hz, C=CHz), 6.78–7.41 (m, Ar—H and C=CHe).

b) 3-Fluorophenylacetaldehyde

Concentrated hydrochloric acid (45 ml) was added to a stirred solution of the preceding enol ether (7.22 g, 47.5 mmol), in THF (225 ml), at 0° C. The mixture was stirred under nitrogen for 0.3 h, at 0° C., and then at room temperature for 3 h. Water was added and the volatiles were evaporated in vacuo. The residue was taken up in diethyl ether and the organic layer separated, washed with water (×2), saturated sodium bicarbonate solution (×1) and water (×1), dried (MgSO$_4$) and evaporated in vacuo to afford the title-aldehyde (5.81 g, 89%), δ (250 MHz, CDCl$_3$) 3.71 (2H, d, J=2.2 Hz, CH$_2$), 6.93–7.39 (4H, m, Ar—H), 9.76 (1H, t, J=2.1 Hz, CHO). This material was used without further purification in the next step.

c) 1-[3-(5-(1,2,4-Triazol-4-yl)-1H-indol-3-yl)propyl]-4-[2-(3-fluorophenyl)ethyl]piperazine. Dihydrogen Maleate. 0.4 Hydrate Acetic acid (3.5 ml, 61.1 mmol) and sodium cyanoborohydride (1.92 g, 30.6 mmol) were added successively to a stirred solution of 1-[3-(5-(1,2,4-triazol-4-yl)-1H-indol-3-yl)propyl]-4(H)-piperazine, in methanol (300 ml), at 0° C. A solution of the preceding aldehyde (4.21 g, 30.5 mmol) in methanol (100 ml) was added dropwise over 0.5 h and the resulting mixture stirred at 0° C. for a further 5 min before being brought up to room temperature. The solution was stirred at room temperature overnight (16.25 h), whereupon TLC (CH$_2$Cl$_2$/MeOH/NH$_3$ 60:8:1) showed formation of a less polar product, although some residual piperazine was also evident. Saturated potassium carbonate solution (150 ml) was added and the solution decanted away from the inorganic solids and evaporated in vacuo. The residue was taken up in ethyl acetate and combined with the inorganic material that had been taken up into water. The organic layer was separated, washed with saturated potassium carbonate solution (×1) and brine (×2), dried (MgSO$_4$) and evaporated in vacuo. Column chromatography of the residue on silica, eluting with CH$_2$Cl$_2$/MeOH/NH$_3$ (80:8:1) afforded the title-indole (8.34 g, 79%). The dihydrogen maleate salt was prepared by addition of a solution of maleic acid (2.87 g, 24.7 mmol) in methanol (12 ml) to a solution of the free base (5.35 g, 12.4 mmol) in methanol (75 ml). The salt precipitated out spontaneously. The mixture was cooled for 15 min, then filtered and the solid washed with diethyl ether (150 ml) and dried in vacuo to afford 7.59 g of material which was recrystallised from boiling methanol (370 ml) to afford the desired product (6.16 g), mp 184° C., (Found C, 58.96; H, 5.69; N, 12.38. C$_{25}$H$_{29}$N$_6$F.2(C$_4$H$_4$O$_4$).0.4H$_2$O requires C, 58.99; H, 5.67; N, 12.51%); HPLC, chemical purity: Rt=6.19 min (98.9%) at λ=230 nm on a Hichrom RPB column, gradient eluting with MeCN in 25 mM phosphate 5 nM PSA, pH3, with a flow rate of 1 ml/min, δ (500 MHz, d$_4$-MeOH+TFA) 2.19–2.25 (2H, m, CH$_2$), 2.91–2.94 (2H, t, J=7.5 Hz, CH$_2$), 3.07–3.11 (2H, m, CH$_2$), 3.29–3.32 (6H, m, 3 of CH$_2$), 3.45–3.48 (2H, m, CH$_2$), 3.70 (4H, br s, 2 of CH$_2$), 6.30 (4H, s, maleate=CH), 7.01–7.10 (3H, m, Ar—H), 7.31–7.41 (3H, m, Ar—H), 7.59 (1H, d, J=8.5 Hz, Ar—H), 7.94 (1H, d, J=2.0 Hz, Ar—H), 9.83 (2H, s, Ar—H).

EXAMPLE 11

1-[3-(5-(Imidazol-1-yl)-1H-indol-3-yl)propyl]-4-[2-(3,4-difluorophenyl)ethyl]piperazine. 2.5 Hydrogen Maleate. 0.3 Hydrate 1. 1-[3-(5-(Imidazol-1-yl)-1H-indol-3-yl)propyl]-4-(H)-piperazine a) 4-(Imidazol-1-yl)nitrobenzene To a stirred solution of imidazole (34.1 g, 0.50 mol) in DMF (300 ml) under Ar, was added portionwise, over 23 minutes, 60% NaH in oil (20.02 g, 0.50 mol). The mixture was then stirred at room temperature for 18 minutes before adding dropwise, over 40 minutes, a solution of 1-fluoro-4-nitrobenzene (70.62 g, 0.50 mol) in DMF (60 ml). The mixture was then stirred at room temperature overnight. Water (600 ml) was then added and the solid was filtered off, washed with water, then stirred in boiling ethyl acetate (400 ml), allowed to cool and filtered, washing the solid with more ethyl acetate (50 ml), then petroleum ether (250 ml). The filtrate, now containing more solid, was refiltered and washed with petroleum ether. The combined solids were dried in a vacuum desiccator overnight to give 90.14 g (95%) of the title compound as a yellow solid. $\delta_H$ (360 MHz, DMSO-$d_6$) 7.19 (1H, t, J=1.1 Hz), 7.97–8.03 (3H, m), 8.38 (2H, d, J=9.2 Hz), 8.52 (1H, t).

b) 4-Imidazol-1-yl)aniline. Dihydrochloride.

A mixture of 4-(imidazol-1-yl)nitrobenzene (89.60 g, 0.474 mol) and 10% palladium on carbon (4.50 g) in ethanol (1200 ml) and 5N HCl (189 ml) was hydrogenated in two batches at 40 psi for 80 minutes. Water (450 ml) was then added to dissolve the product and the catalyst was removed by filtration, washed with more water, and the combined filtrates were evaporated in vacuo, using finally a freeze drier, to give 105.4 g (96%) of the title compound as a cream solid. $\delta_H$ (250 MHz, $D_2O$) 7.22 (2H, d, J=8.8 Hz), 7.35 (1H, t, J=2.1 Hz), 7.44 (2H, d, J=9.0 Hz), 7.59 (1H, t, J=1.8 Hz), 8.89 (1H, t, J=1.5 Hz).

c) 4-(Imidazol-1-yl)phenplhydrazine. Dihydrochloride.

To a cooled (−15° C.) and stirred suspension of 4-(imidazol-1-yl)aniline dihydrochloride (20 g, 86.16 mmol) in concentrated hydrochloric acid (100 ml) was added dropwise, over 1 hour, a solution of sodium nitrite (6.25 g, 9.05 mmol) in water (40 ml). After a further 10 minutes of stirring at −12° C., the mixture was quickly filtered to remove a solid, and the filtrate was added portionwise to a cooled (−20° C.) and stirred solution of tin (II) chloride dihydrate (100 g) in concentrated hydrochloric acid (50 ml) at such a rate as to maintain the internal temperature below −10° C. (15 minutes). The mixture was allowed to warm to 5° C. over 30 minutes, and the solid was collected and washed with diethyl ether (4×100 ml). The above solid was suspended in water (200 ml) and basified with 4N sodium hydroxide solution and extracted with ethyl acetate (5×500 ml). The combined organic solutions were dried ($Na_2SO_4$) and filtered. The filtrate was vigorously stirred while hydrogen chloride was being bubbled through the solution until a deep red mixture was obtained. Stiring was continued for a further 20 minutes to give a cream solid which was collected by filtration and dried over phosphorus pentoxide-potassium hydroxide under high vacuum to leave 12.7 g (60%) of the title compound; $\delta_H$ (360 MHz, DMSO-$d_6$) 7.20 (2H, d, J=9.0 Hz), 7.73 (2H, d, J=9.0 Hz), 7.91 (1H, t, J=1.5 Hz), 8.23 (1H, t, J=1.7 Hz), 9.71 (1H, t, J=1.3 Hz).

d) 1-[3-(5-(Imidazol-1-yl)-1H-indol-3-yl)propyl]-4-(H)-piperazine

Prepared from 4-(imidazol-1-yl)phenylhydrazine and 5-(4-tert-butyloxycarbonyl)piperazin-1-yl pentanal dimethyl acetal using the procedure described for Example 1, Intermediate 2, δ (250 MHz, $D_6$-DMSO) 1.86–1.97 (2H, m, $CH_2$), 2.37–3.66 (12H, m, 6 of $CH_2$), 4.23 (1H, br s, NH), 7.20 (1H, s, Ar—H), 7.35–7.40 (2H, m, Ar—H), 7.56 (1H, d, J=8.6 Hz, Ar—H), 7.77 (1H, d, J=2.0 Hz, Ar—H), 7.80 (1H, d, J=2.0 Hz, Ar—H), 8.24 (1H, s, Ar—H), 11.11 (1H, s, NH).

2. 1-[3-(5-(Imidazol-1-yl)-1H-indol-3-yl)propyl]-4-[2-(3,4-difluorophenyl)ethyl]piperazine. 2.5 Hydrogen Maleate. 0.3 Hydrate The title compound was prepared from 3,4-difluorophenylacetaldehyde and 1-[3-(5-(imidazol-1-yl)-1H-indol-3-yl)propyl]-4-(H)-piperazine using the procedure described in Example 10. The 2.5 hydrogen maleate 0.3 hydrate salt was prepared, mp 143° C., (Found: C, 58.07; H, 5.19; N, 9.39. $C_{26}H_{29}N_5F_2$. 2.5($C_4H_4O_4$). 0.3$H_2O$ requires C, 58.03; H, 5.26; N, 9.40%), m/e 450 (M+1)$^+$, δ (360 MHz, $D_6$-DMSO) 1.96–2.06 (2H, m, $CH_2$), 2.50–3.70 (16H, m, 8 of $CH_2$), 6.12 (maleate-H's), 7.06–7.10 (1H, m, Ar—H), 7.28–7.38 (4H, m, Ar—H), 7.52 (1H, d, J=8.6 Hz, Ar—H), 7.54 (1H, s, Ar—H), 7.83 (1H, d, J=2.0 Hz, Ar—H), 7.97 (1H, d, J=2.0 Hz, Ar—H), 8.91 (1H, s, Ar—H), 11.19 (1H, s, NH).

EXAMPLE 12

1-[3-(5-Imidazol-1-yl)-1H-indol-3-yl)propyl]-4-[2-(3-fluorophenyl)ethyl]piperazine. 2.5 Hydrogen Maleate. Hemihydrate Prepared from 1-[3-(5-(imidazol-1-yl)-1H-indol-3-yl)propyl]-4-(H)-piperazine and 3-fluorophenylacetaldehyde using the procedure described for Example 10. The 2.5 hydrogen maleate hemihydrate salt was prepared, mp 158°–159° C., (Found: C, 59.16; H, 5.62; N, 9.71. $C_{26}H_{30}N_5F$. 2.5($C_4H_4O_4$).0.5$_2O$ requires C, 59.17; H, 5.66; N, 9.58%), m/e 432 (M+1)$^+$, δ (250 MHz, $D_6$-DMSO) 1.90–2.08 (2H, m, $CH_2$), 2.54–3.60 (16H, m, 8 of $CH_2$), 6.11 (maleate-H's), 6.98–7.15 (3H, m, Ar—H), 7.29–7.39 (3H, m, Ar—H), 7.51–7.54 (2H, m, Ar—H), 7.84 (1H, d, J=2.0 Hz, Ar—H), 7.97 (1H, s, Ar—H), 8.90 (1H, s, Ar—H), 11.20 (1H, s, NH).

Examples 13 and 14 were prepared from 1-[3-(5-(2-methylimidazol-1-yl)-1H-indol-3-yl)propyl]-4-(H)-piperazine and the appropriate phenylacetaldehyde using the procedures described for Example 11.

EXAMPLE 13

1-[3-(5-(2-Methylimidazol-1-yl)-1H-indol-3-yl)propyl]-4-[2-(3-fluorophenyl)ethyl]piperazine. 2.75 Hydrogen Maleate mp: 160°–161° C., (Found: C, 59.52; H, 5.74; N, 9.46. $C_{27}H_{32}N_5F$. 2.75($C_4H_4O_4$) requires C, 59.68; H, 5.67; N, 9.16%), m/e 446 (M+1)$^+$, δ (250 MHz, $D_6$-DMSO) 1.88–2.06 (2H, m, $CH_2$), 2.54–3.60 (16H, m, 8 of $CH_2$), 6.08 (maleate-H's), 6.98–7.40 (6H, m, Ar—H), 7.56 (1H, d, J=8.6 Hz, Ar—H), 7.70 (1H, d, J=2.0 Hz, Ar—H), 7.75 (1H, d, 2.0 Hz, Ar—H), 7.80 (1H, d, J=2.0 Hz, Ar—H), 11.33 (1H, s, NH).

EXAMPLE 14

1-[3-(5-(2-Methylimidazol-1-yl)-1H-indol-3-yl)propyl]-4-[2-(3,4-difluorophenyl)ethyl]piperazine. 2.75 Hydrogen Maleate mp: 148°–149° C., (Found: C, 58.29; H, 5.51; N, 8.72. $C_{27}H_{31}N_5F_2$. 2.75($C_4H_4O_4$) requires C, 58.31; H, 5.41; N, 8.95%), m/e 464 (M+1)$^+$, δ (250 MHz, $D_6$-DMSO) 1.88–2.06 (2H, m, $CH_2$), 2.52–3.60 (16H, m, 8 of $CH_2$), 6.09 (maleate-H's), 7.06–7.14 (1H, m, Ar—H), 7.25 (1H, dd, J=8.6 and 2.0 Hz, Ar—H),7.30–7.42 (3H, m, Ar—H), 7.57 (1H, d, J=8.6 Hz, Ar—H), 7.71 (1H, d, J=2.0 Hz, Ar—H), 7.76 (1H, d, J=2.0 Hz, Ar—H), 7.79 (1H, d, J=2.0 Hz, Ar—H), 11.34 (1H, s, NH).

EXAMPLE 15

1-[3-(5-(1,2,4-Triazol-1-ylmethyl)-1H-indol-3-yl)propyl]-4-[2-(3-fluorophenyl)ethyl]piperazine. Dihydrogen Maleate 1. 3-[5-(1,2,4-Triazol-1-ylmethyl)-1H-indol-3-yl]propan-1-ol 3,4-Dihydro-2H-pyran (3.9 ml, 42.7 mmol) was added to a stirred solution of 4-(1,2,4-triazol-1-ylmethyl)phenyl hydrazine (EP 497,512; 4.0 g, 21.1 mmol) in dioxane/water/5N HCl (38 ml/14 ml/4.7 ml) and stirred at room temperature for 1.75 h. The solution was then refluxed for 1.5 h and the solvent removed under vaccum. The residue was taken up into $CH_2Cl_2$ and saturated aqueous $K_2CO_3$ solution. The aqueous was separated and further extracted with $CH_2Cl_2$ (×4). The combined organic extracts were dried ($MgSO_4$) and evaporated and the residue chromatographed on silica gel eluting with $CH_2Cl_2/MeOH/NH_3$ (80:8:1) to give the title-indole (0.919 g, 17%), δ (250 MHz, $CDCl_3$) 1.91–2.03 (2H, m, $CH_2$), 2.84 (2H, t, J=7.9 Hz, $CH_2$), 3.73 (2H, t, J=7.9 Hz, $CH_2$), 5.43 (2H, s, $CH_2$), 7.04 (1H, d, J=2.3 Hz, Ar—H), 7.11 (1H, dd, J=2.3 and 8.3 Hz, Ar—H), 7.35 (1H, d, J=8.3 Hz, Ar—H), 7.58 (1H, s, Ar—H), 7.97 (1H, s, Ar—H), 8.02 (1H, s, Ar—H), 8.18 (1H, s, NH).

2. 4-[2-(3-Fluorophenyl)ethyl]piperazine

Sodium cyanoborohydride (2.95 g, 47.03 mmol) was added portionwise to a solution of N-BOC-piperazine (4.38 g, 23.52 mmol) and glacial acetic acid (4.24 g, 70.55 mmol), in methanol (200 ml), at −10° C. A solution of 3-fluorophenylacetaldehyde (3.89 g, 28.23 mmol) in methanol (20 ml) was added dropwise and the mixture then warmed to +25° C. and stirred for 16 h. The solution was basified with saturated $K_2CO_3$ solution and the methanol removed under vacuum. The aqueous was extracted with $CH_2Cl_2$ (2×200 ml) and the combined extracts washed with brine (×2), dried ($Na_2SO_4$) and evaporated to give 5.29 g of product (73%). Formic acid (100 ml) was added to the preceding adduct (4.84 g, 15.7 mmol) and the solution stirred at room temperature for 16 h. The solvent was removed under vacuum, the residue basified by addition of saturated $K_2CO_3$ solution, and extracted into n-butanol (50 ml). The butanol was removed under vacuum and the residue chromatographed on silica gel eluting with $CH_2Cl_2/MeOH/NH_3$ (40:8:1) to give the title-product (2.35 g, 72%), δ (360 MHz, $CDCl_3$) 2.50 (4H, br s, 2 of $CH_2$), 2.56–2.63 (2H, m, $CH_2$), 2.78–2.83 (2H, m, $CH_2$), 2.92–2.94 (4H, m, 2 of $CH_2$), 6.86–6.99 (3H, m, Ar—H), 7.20–7.27 (1H, m, Ar—H).

3. 1-[3-(5-(1,2,4-Triazol-1-ylmethyl)-1H-indol-3-yl)propyl]-4-[2-(3-fluorophenyl)ethyl]piperazine. Dihydrogen Maleate Methanesulphonyl chloride (0.118 g, 1.03 mmol) was added to a stirred solution of 3-[5-(1,2,4-triazol-1-ylmethyl)-1H-indol-3-yl]propan-1-ol (0.22 g, 0.86 mmol) and triethylamine (0.104 g, 1.03 mmol), in anhydrous THF (30 ml) at +5° C. The solution was warmed to room temperature and stirred for 1.5 h. The solvent was removed under vacuum and the residue partitioned between $CH_2Cl_2$ (2×75 ml) and water (30 ml). The combined extracts were dried ($Na_2SO_4$) and evaporated and the residue redissolved in anhydrous THF (20 ml). To the solution was added 4-[2-(3-fluorophenyl)ethyl]piperazine (0.339 g, 1.63 mmol), $K_2CO_3$ (0.225 g, 1.63 mmol) and sodium iodide (0.245 g, 1.63 mmol) and the mixture refluxed for 2 h. The solvent was removed under vacuum and the residue partitioned between $CH_2Cl_2$ (2×100 ml) and water (40 ml). The combined extracts were dried ($Na_2SO_4$) and evaporated and the resulting residue chromatographed on silica gel eluting with $CH_2Cl_2/EtOH/NH_3$ (80:5:0.5) to give the title-indole (0.269 g, 70%). The dihydrogen maleate salt was prepared, mp 187° C., (Found: C, 60.01; H, 5.63; N, 12.12. $C_{26}H_{31}N_6F$. $2(C_4H_4O_4)$ requires C, 60.17; H, 5.79; N, 12.38%), m/e 447 (M+1)$^+$, δ (360 MHz, $D_6$-DMSO) 1.90–2.02 (2H, m, $CH_2$), 2.54–3.70 (16H, m, 8 of $CH_2$), 5.44 (2H, s, $CH_2$), 6.14 (maleate-H's), 7.00–7.14 (4H, m, Ar—H), 7.19 (1H, s, Ar—H), 7.31–7.36 (2H, m, Ar—H), 7.52 (1H, s, Ar—H), 7.95 (1H, s, Ar—H), 8.60 (1H, s, Ar—H), 10.90 (1H, s, NH).

EXAMPLE 16

1-[3-(5-(1,2,4-Triazol-1-ylmethyl)-1H-indol-3-yl)propyl]-4-[2-(3,4-difluorophenyl)ethyl]perazine. Dihydrogen Maleate The title compound was prepared from 3-[5-(1,2,4-triazol-1-ylmethyl)-1H-indol-3-yl]propan-1-ol and 4-[2-(3,4-difluorophenyl)ethyl]piperazine using the procedures described for Example 15. The dihydrogen maleate salt was prepared, mp 178°–179° C., (Found: C, 58.43; H, 5.43; N, 12.04. $C_{26}H_{30}N_6F_2$. $2.0(C_4H_4O_4)$ requires C, 58.61; H, 5.50; N, 12.06%), m/e 465 (M+1)$^+$, δ (250 MHz, $CDCl_3$ on free base) 1.88–2.04 (2H, m, $CH_2$), 2.38–2.82 (16H, m, 8 of $CH_2$), 5.43 (2H, d, $CH_2$), 6.86–7.16 (5H, m, Ar—H), 7.36 (1H, d, J=8.4 Hz, Ar—H), 7.57 (1H, s, Ar—H), 7.96 (1H, s, Ar—H), 8.00 (1H, s, Ar—H), 8.11 (1H, br s, NH).

EXAMPLE 17

1-[3-(5-(1,2,4-Triazol-4-yl)-1H-indol-3-yl)propyl]-4-[2-(3-fluorophenyl)-ethyl]piperazine. dicitrate salt 1-[3-(5-(1,2,4-Triazol-4-yl)-1H-indol-3-yl)propyl]-4-[2-(3-fluorophenyl)ethyl]piperazine was dissolved in methanol heated to 58° C. under a nitrogen atmosphere. Citric acid, in methanol at 58° C., was added, and the solution allowed to cool to ambient temperature, then left to stand for 16 hours. The mixture was filtered and the solid dried in vacuo at 50° C. to give the title compound, mp 176° C. (dec.).

What is claimed is:

1. A compound of formula I, or a pharmaceutically acceptable salt thereof:

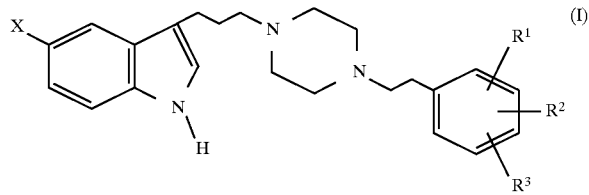

wherein

X represents a group of formula (Xa), (Xb) or (Xc):

-continued

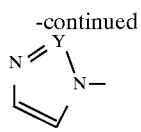
(Xc)

in which Y represents nitrogen or C—R$_4$;

R$^1$ represents fluoro, chloro, trifluoromethyl, C$_{1-6}$ alkoxy or a group of formula (a):

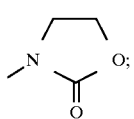
(a)

R$^2$ and R$^3$ independently represent hydrogen, halogen, trifluoromethyl or C$_{1-6}$ alkoxy; and R$^3$ represents hydrogen or C$_{1-6}$ alkyl.

2. A compound as claimed in claim 1 wherein X represents a group of formula (Xa).

3. A compound as claimed in claim 1 or claim 2 represented by formula IIA, and pharmaceutically acceptable salts thereof:

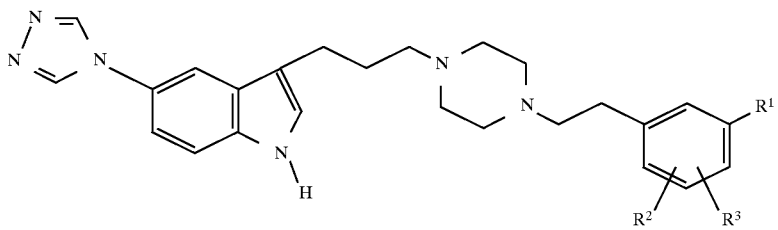
(IIA)

wherein R$^1$, R$^2$ and R$^3$ are as defined in claim 1.

4. A compound as claimed in claim 1 represented by formula IIB, and pharmaceutically acceptable salts thereof:

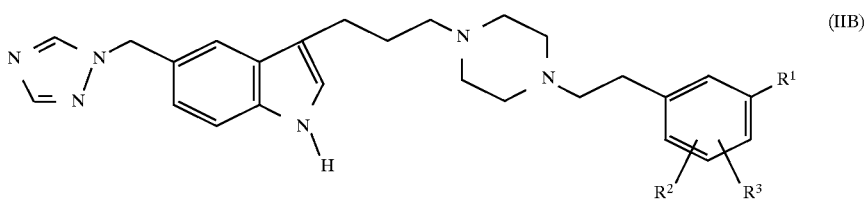
(IIB)

wherein R$^1$, R$^2$ and R$^3$ are as defined in claim 1.

5. A compound as claimed in claim 1 represented by formula IIC, and pharmaceutically acceptable salts thereof:

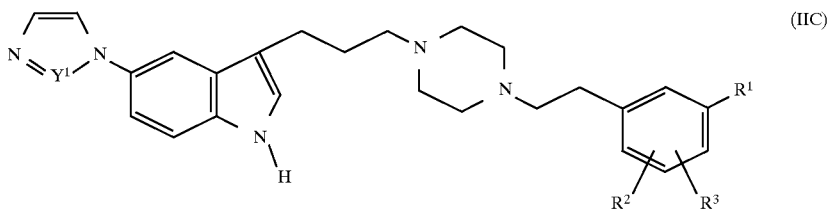
(IIC)

wherein Y$^1$ represents nitrogen, CH or C-methyl; and R$^1$, R$^2$ and R$^3$ are as defined in claim 1.

6. A compound as claimed in claim 1 wherein R$^1$ represents fluoro or trifluoromethyl.

7. A compound as claimed in claim 1 wherein R$^2$ and R$^3$ independently represent hydrogen or fluoro.

8. A compound as claimed in claim 1 wherein R$^2$ is hydrogen and R$^3$ is other then hydrogen.

9. A compound as claimed in claim 1 wherein R$^2$ and R$^3$ are both hydrogen.

10. A compound selected from:
1-[3-(5-(1,2,4-triazol-4-yl)-1H-indol-3-yl)propyl]-4-[2-(3-fluorophenyl)-ethyl]piperazine;
1-[3-(5-(1,2,4-triazol-4-yl)-1H-indol-3-yl)propyl]-4-[2-(2-fluorophenyl)-ethyl]piperazine;
1-[3-(5-(1,2,4-triazol-4-yl)-1H-indol-3-yl)propyl]-4-[2-(4-fluorophenyl)-ethyl]piperazine;
1-[3-(5-(1,2,4-triazol-4-yl)-1H-indol-3-yl)propyl]-4-[2-(3-methoxyphenyl)-ethyl]piperazine;
1-[3-(5-(1,2,4-triazol-4-yl)-1H-indol-3-yl)propyl]-4-[2-(3-trifluoromethylphenyl)ethyl]piperazine;
1-[3-(5-(1,2,4-triazol-4-yl)-1H-indol-3-yl)propyl]-4-[2-(3,4-difluorophenyl)-ethyl]piperazine;
1-[3-(5-(1,2,4-triazol-4-yl)-1H-indol-3-yl)propyl]-4-[2-(2,4-difluorophenyl)-ethyl]piperazine;
1-[3-(5-(1,2,4-triazol-4-yl)-1H-indol-3-yl)propyl]-4-[2-(3,5-difluorophenyl)-ethyl]piperazine;
1-[3-(5-(1,2,4-triazol-4-y)-1H-indol-3-yl)propyl]-4-[2-(3-(oxazolidin-2-on-3-yl)phenyl)ethyl]piperazine;

and pharmaceutically acceptable salts thereof.

11. A compound selected from:

1-[3-(5-(imidazol-1-yl)-1H-indol-3-yl)propyl]-4-[2-(3,4-difluorophenyl)-ethyl]piperazine;

1-[3-(5-(imidazol-1-yl)-1H-indol-3-yl)propyl]-4-[2-(3-fluorophenyl)-ethyl]piperazine;

1-[3-(5-(2-methylimidazol-1-yl)-1H-indol-3-yl)propyl]-4-[2-(3-fluorophenyl)ethyl]piperazine;

1-[3-(5-(1,2,4-triazol-1-ylmethyl)-1H-indol-3-yl)propyl]-4-[2-(3,4-difluorophenyl)ethyl]piperazine;

1-[3-(5-(2-methylimidazol-1-yl)-1H-indol-3-yl)propyl]-4-[2-(3,4-difluorophenyl)ethyl]piperazine;

1-[3-(5-(1,2,4-triazol-1-ylmethyl)-1H-indol-3-yl)propyl]-4-[2-(3-fluorophenyl)ethyl]piperazine;

and pharmaceutically acceptable salts thereof.

12. 1-[3-(5-(1,2,4-Triazol-4-yl)-1H-indol-3-yl)propyl]-4-[2-(3-fluorophenyl)ethyl]piperazine, or a pharmaceutically acceptable salt thereof.

13. A salt of the compound as claimed in claim 12 selected from the group consisting of the oxalate, maleate and citrate salts.

14. The dicitrate salt of 1-[3-(5-(1,2,4-triazol-4-yl)-1H-indol-3-yl)propyl]-4-[2-(3-fluorophenyl)ethyl]piperazine.

15. A pharmaceutical composition comprising a compound of formula I as defined in claim 1 or a pharmaceutically acceptable salt thereof in association with a pharmaceutically acceptable carrier.

16. A process for the preparation of a compound as claimed in claim 1, which comprises:

(A) reacting a compound of formula III with a compound of formula IV:

(III)

(IV)

wherein X, $R^1$, $R^2$ and $R^3$ are as defined in claim 1, and $L^1$ represents a suitable leaving group; or (B) reacting a compound of formula III as defined above with a compound of formula V:

(V)

wherein $R^1$, $R^2$ and $R^3$ are as defined in claim 1; in the presence of a reducing agent; or (C) reacting a compound of formula III as defined above with a carboxylic acid derivative of formula VI:

(VI)

wherein $R^1$, $R^2$ and $R^3$ are as defined in claim 1; in the presence of a condensing agent; followed by treatment with a reducing agent; or (D) reacting the appropriate compound of formula VII:

(VII)

wherein X is as defined in claim 1; with a compound of formula XII, or a carbonyl-protected form thereof:

(XII)

wherein $R^1$, $R^2$ and $R^3$ are as defined in claim 1; or (E) reacting a compound of formula XIV:

(XIV)

wherein $R^1$, $R^2$ and $R^3$ are as defined in claim 1; with a compound of formula XV:

(XV)

wherein X is as defined in claim 1 and $L^3$ is a suitland leaving group; or (F) reducing a compound of formula XVIII:

(XVIII)

wherein X, $R^1$, $R^2$ and $R^3$ are as defined in claim 1.

17. A method for the treatment and/or prevention of migraine, cluster headache, chronic paroxysmal hemicrania, headache associated with vascular disorders, tension headache and paediatric headache, which method comprises administering to a patient in need of such treatment an effective amount of a compound of formula I as defined in claim 1 or a pharmaceutically acceptable salt thereof.

* * * * *

UNITED STATES PATENT AND TRADEMARK OFFICE
CERTIFICATE OF CORRECTION

PATENT NO. : 5,889,008

DATED : March 30, 1999

INVENTOR(S) : R. A. Jelley, A. M. MacLeod, A. J. Reeve, F. Sternfeld, and L. J. Street It is certified that error appears in the above-identified patent and that said Letters Patent is hereby corrected as shown below:

1) On the title page, add:

[45] *Mar. 30, 1999

[ * ] Notice: The term of this patent shall not extend beyond the expiration date of Pat. No. 5,807,857.

2) In the Title of the Invention, delete:

"4-PHENETHYLPIPERAZADINE" and insert in its place -- 4-PHENETHYLPIPERAZINE- --.

UNITED STATES PATENT AND TRADEMARK OFFICE
CERTIFICATE OF CORRECTION

PATENT NO. : 5,889,008
DATED : March 30, 1999
INVENTOR(S) : R. A. Jelley, A. M. MacLeod, A. J. Reeve, F. Sternfeld, and L. J. Street It is certified that error appears in the above-identified patent and that said Letters Patent is hereby corrected as shown below:

3) In the Abstract, at line 10, delete "5-HT$_{1D\alpha}$" and insert in its place -- 5-HT$_{1D\beta}$ --.

4) In Column 1, in the Title of the Invention, delete "4-PHENETHYLPIPERAZADINE" and insert in its place -- 4-PHENETHYLPIPERAZINE --.

Signed and Sealed this

Third Day of August, 1999

Attest:

Q. TODD DICKINSON

*Attesting Officer*    Acting Commissioner of Patents and Trademarks